United States Patent [19]
Quantrille et al.

[11] Patent Number: 5,804,286
[45] Date of Patent: Sep. 8, 1998

[54] EXTENSIBLE COMPOSITE NONWOVEN FABRICS

[75] Inventors: Thomas E. Quantrille, Simpsonville; Harold E. Thomas, Greer; Barry D. Meece, Pelzer, all of S.C.; Scott L. Gessner, Encinitas, Calif.; J. Darrell Gillespie, Simpsonville, S.C.; Jared A. Austin; David D. Newkirk, both of Greer, S.C.; William Fowells, Washougal, Wash.

[73] Assignee: Fiberweb North America, Inc., Simpsonville, S.C.

[21] Appl. No.: 676,360

[22] PCT Filed: Nov. 22, 1995

[86] PCT No.: PCT/US95/15257

§ 371 Date: Aug. 27, 1996

§ 102(e) Date: Aug. 27, 1996

[87] PCT Pub. No.: WO96/16216

PCT Pub. Date: May 30, 1996

[51] Int. Cl.⁶ .................. B32B 5/26; B32B 7/10; B32B 7/14
[52] U.S. Cl. .................. 428/198; 428/200; 428/373; 442/36; 442/328; 442/329; 442/346; 442/347; 442/350; 442/361; 442/365; 442/389; 442/394; 442/398; 442/399; 604/370; 604/372; 604/385.2

[58] Field of Search ................ 428/198, 200, 428/373; 442/36, 328, 329, 346, 347, 350, 361, 365, 389, 394, 398, 399; 604/370, 372, 385.2

[56] References Cited

U.S. PATENT DOCUMENTS

| | | |
|---|---|---|
| 4,874,666 | 10/1989 | Kubo et al. . |
| 5,108,827 | 4/1992 | Gessner . |
| 5,593,768 | 1/1997 | Gessner ................ 442/346 |
| 5,645,057 | 7/1997 | Watt ................ 442/346 |

*Primary Examiner*—James C. Cannon
*Attorney, Agent, or Firm*—Bell Seltzer Intellectual Property Law Group of Alston & Bird, LLP

[57] ABSTRACT

A fabric comprising at least two layers wherein at least one layer is an extensible, bonded non-woven composed of a fiber comprising multiple different polymers such as a fiber comprising isotactic polypropylene, polyethylene and a block or grafted polyolefin copolymer or terpolymer which is at least partially miscible with said polypropylene and polyethylene.

61 Claims, 2 Drawing Sheets

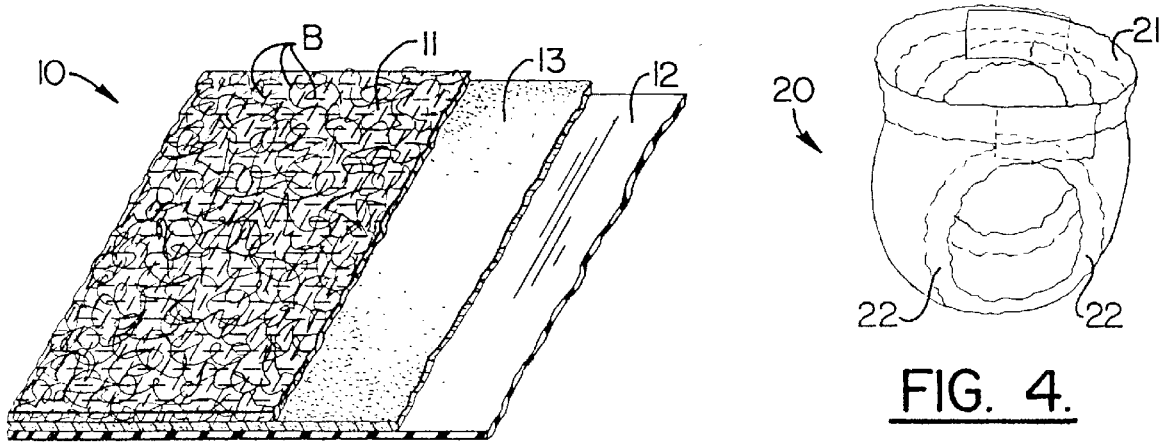
FIG. 1.
FIG. 4.
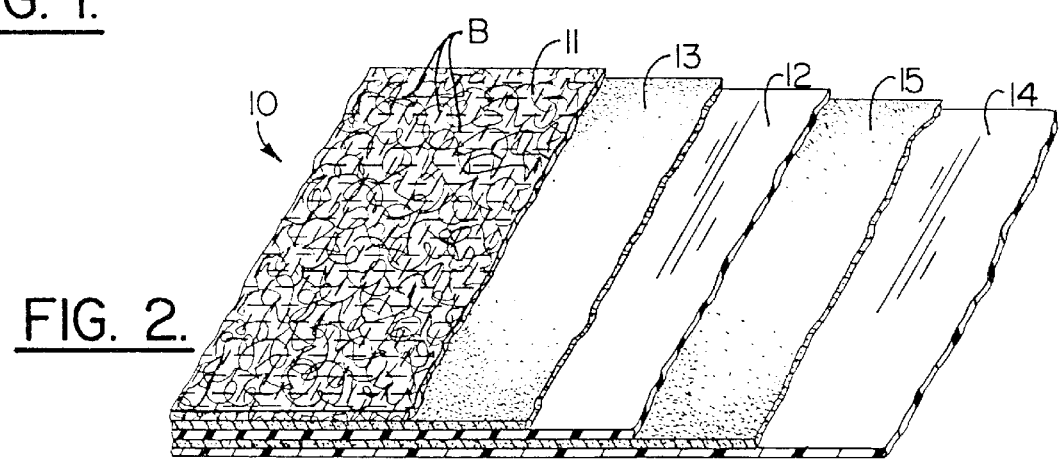
FIG. 2.
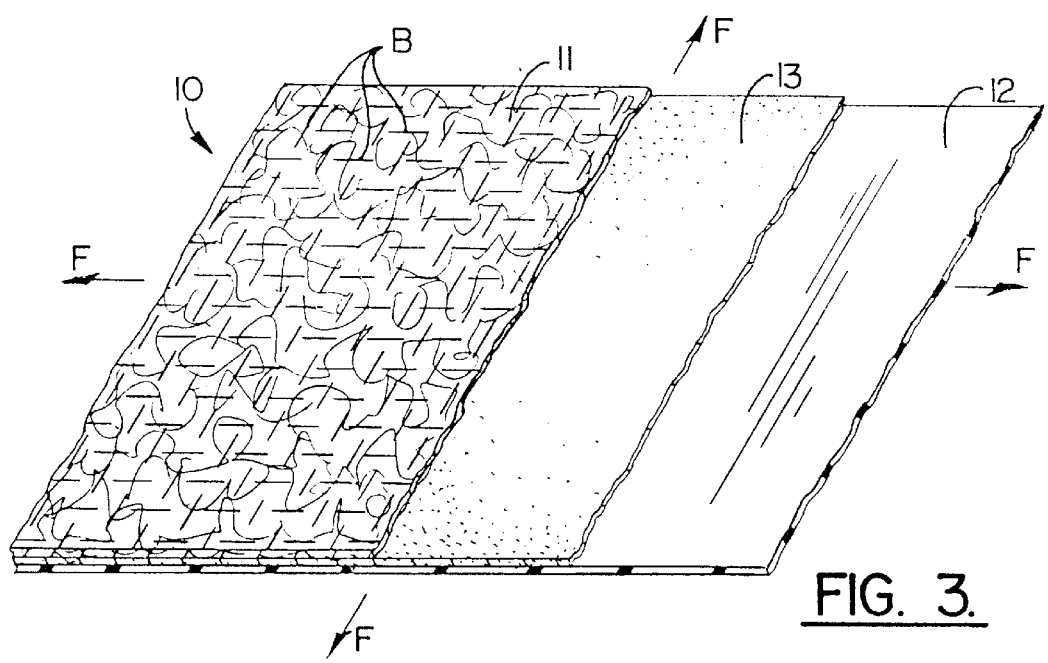
FIG. 3.

EXTENSIBLE COMPOSITE NONWOVEN FABRICS

FIELD OF THE INVENTION

The invention relates to composite nonwoven fabrics, and more particularly to extensible nonwoven composite fabrics which are capable of elongating during mechanical stretching and which have excellent surface abrasion resistance.

BACKGROUND OF THE INVENTION

Composite nonwoven fabrics are used in a variety of applications such as garments, disposable medical products, diapers and personal hygiene products. New products being developed for these applications have demanding performance requirements, including comfort, conformability to the body, freedom of body movement, good softness and drape, adequate tensile strength and durability, and resistance to surface abrasion, pilling or fuzzing. Accordingly, the composite nonwoven fabrics which are used in these types of products must be engineered to meet these performance requirements.

In Sabee, U.S. Pat. Nos. 4,153,664 and 4,223,063, it is disclosed that the softness and drapeability of composite nonwoven fabrics, formed for example from a meltblown or a spunbonded nonwoven fabric, can be improved by drawing or stretching the fabric. More particularly, according to Sabee, the composite nonwoven fabrics are processed by differentially drawing or stretching the web to form a quilted pattern of drawn and undrawn areas, providing a product with enhanced softness, texture and drapeability. However, while the stretching may improve some fabric physical properties, it can adversely affect other important properties, such as abrasion resistance, for example, leaving the fabric with an unsightly fuzzed surface. In addition, Sabee teaches the use of undrawn or underdrawn filaments in the use of this application. Undrawn or underdrawn filaments are typically higher in denier and therefore the fabrics tend to be stiff.

Often, the performance requirements of the product demand a composite nonwoven fabric having elasticity. In certain disposable diaper designs, for example, it is desired to impart elastic properties to the waist and/or to the leg cuff areas. One approach which has been taken to providing such elastic properties in a composite nonwoven fabric involves forming and stretching an elastic web, then bonding a gatherable web to the elastic web, and relaxing the composite. An obvious limitation of this approach is having to form the composite in the tensioned state. This requires additional equipment and control systems. Examples of this process are Mormon, U.S. Pat. No. 4,657,802, where it is disclosed that a composite nonwoven elastic is made by first stretching an elastic web, forming a fibrous nonwoven gatherable web onto the stretched elastic nonwoven, joining the two together to form a composite structure, then allowing the composite to relax. In Collier, et al., U.S. Pat. No. 5,169,706, it is disclosed that a composite elastic material having a low stress relaxation is formed between an elastic sheet and a gatherable layer. In Daponte, U.S. Pat. No. 4,863,779, a composite is disclosed which involves first tensioning the elastic elastic web to elongate it, bonding at least one gatherable web to the elastic web, and relaxing the composite immediately after bonding, so that the gatherable web is gathered between the bond points.

Another approach to imparting elastic properties to a composite nonwoven fabric is with a so-called "zero-strain" stretchable laminate. A "zero-strain" stretchable laminate refers to a fabric in which at least two layers of material, one elastic, the other substantially inelastic, are secured to one another along their coextensive surfaces while in a substantially untensioned state. The fabric is subsequently subjected to mechanical stretching. The inelastic layer typically fractures or extends, thus permanently elongating the inelastic layer and producing a composite fabric with elastic properties. This lamination and stretching process is advantageous in that utilizing elastic in an unstretched condition is easier and less expensive than stretched elastic used in traditional processing operations. However, one problem which has existed with presently available "zero-strain" stretchable laminates is surface abrasion. The mechanical stretching either fractures or disrupts the fibers within the substantially inelastic component of the "zero-strain" laminate, and as a result, the fibers detach and are susceptible to linting and pilling. In addition, such fracturing or detachment causes a noticeable loss in fabric strength.

There have been attempts to address the aforementioned problems of fiber tie down and fabric abrasion resistance. For example, attempts have been made to make the nonwoven fabric component of the composite with high elongation properties. Conventional polypropylene, which has been widely used in producing nonwoven fabrics, provides adequate fuzz and abrasion resistance properties in the unstretched condition, but the elongation properties are unacceptable and therefore the fibers and/or fabrics fracture. Nonwoven webs formed from linear low density polyethylene (LLDPE) have been shown to have high elongation properties and also to possess excellent hand, softness and drape properties, as recognized for example in Fowells U.S. Pat. No. 4,644,045. However, such fabrics have not found wide commercial acceptance, since they fail to provide acceptable abrasion resistance. The bonding of LLDPE filaments into a spunbonded web with acceptable abrasion resistance has proven to be very difficult, since acceptable fiber tie down is observed at a temperature just below the point that the filaments begin to melt and stick to the calender. Because of this very narrow bonding window and the resulting abrasion resistance and fuzz properties, spunbonded LLDPE nonwovens have not found wide commercial acceptance for the aforementioned applications.

SUMMARY OF THE INVENTION

The present invention overcomes these disadvantages and limitations and provides a composite fine denier nonwoven fabric with a superior combination of extensibility, tensile properties and abrasion resistance. The composite nonwoven fabric of the present invention is comprised of at least two layers, the first layer containing multipolymer fibers with a plurality of bonds bonding the fibers together to form a coherent extensible nonwoven web. This coherent extensible nonwoven web has a Taber surface abrasion value (rubber wheel) of greater than 10 cycles and an elongation at peak load in at least one of the machine direction or the cross-machine direction of at least 70%. A second extensible layer is laminated to this coherent extensible nonwoven web.

The term "fibers" as used herein is intended to include both discrete length "staple" fibers and continuous filaments. According to one embodiment of the present invention, the coherent extensible nonwoven web is a thermally bonded spunbond nonwoven web of randomly arranged substantially continuous filaments consisting of multiple polymers. According to another embodiment of the invention, the coherent extensible nonwoven web is a thermally bonded carded web of staple fibers. The coherent extensible nonwoven web may contain, in addition to the multipolymer fibers, additional fibrous components, such as meltblown microfibers. In accordance with the invention, the composite nonwoven fabric may include an optional third component laminated to the opposite side of the second extensible layer, which may, for example, be a film, another nonwoven web, or a composite fabric.

The second extensible layer to which the multipolymer fiber web is laminated can take various forms. For example, it may comprise a continuous or perforated polymer film, a film or web of an elastic polymer, another spunbonded nonwoven web, an extensible scrim or net, an array of extensible or elastic strands, or a web of meltblown microfibers. Where an elastic web or film is used, the composite can be stretch activated by elongation, which causes permanent elongation and stretching of the coherent extensible web of multipolymer fibers, and the resulting composite fabric exhibits elastic properties. Where an extensible nonelastic film layer is used, such as polyolefin film for example, the composite can be stretch activated by elongation to at least 20% of its original unstretched length, producing a composite having excellent softness and drape.

BRIEF DESCRIPTION OF THE DRAWINGS

Some of the features and advantages of the invention having been stated, others will become apparent from the detailed description which follows, and from the accompanying drawings, in which:

FIG. 1 is a schematic perspective view showing a nonwoven composite fabric in an unstretched state, with the layers and bonds being exaggerated for clarity of illustration;

FIG. 2 is a perspective view showing a composite nonwoven fabric similar to FIG. 1 with an additional extensible layer being incorporated into the composite fabric;

FIG. 3 is a perspective view showing the composite fabric of FIG. 1 being elongated by mechanical stretching;

FIG. 4 is a side view of a diaper incorporating the composite fabric of this invention.

DETAILED DESCRIPTION OF THE PREFERRED EMBODIMENTS

Figure 5A:
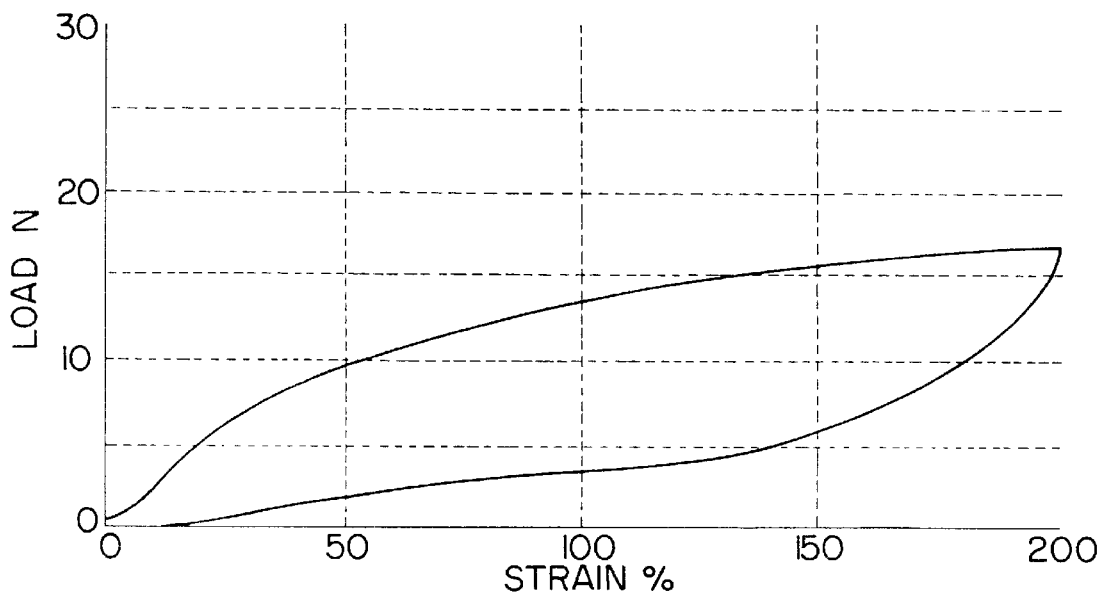
FIGS. 5A and 5B are graphs showing the stress-strain relationships of the fabric sample described in Example 11 after a first and second elongation, respectively.

FIG. 1 shows a composite nonwoven fabric in accordance with the present invention. As depicted, the composite 10 includes an extensible, nonelastic, nonwoven web 11 of multipolymer fibers laminated to a second extensible layer 12 by an adhesive layer 13. By "extensible nonelastic", it is meant that the web 11 can be relatively easily stretched beyond its elastic limit and permanently elongated by application of tensile stress. However, the web has little retractive force and is therefore nonelastic. The extensible nonelastic nonwoven web 11 comprises a layer of multipolymer fibers and a plurality of bonds B bonding the fibers together to form a nonwoven web which is coherent and extensible. The web 11 may be made by any of a number of manufacturing techniques well known in the nonwovens field.

For example, according to one embodiment of the invention, the coherent extensible nonwoven web 11 is a thermally bonded spunbond nonwoven web of randomly arranged substantially continuous filaments. The spunbond nonwoven web may be produced, for example, by the conventional spunbond process wherein molten polymer is extruded into continuous filaments which are subsequently quenched, attenuated by a high velocity fluid, and collected in random arrangement on a collecting surface. After filament collection, any thermal, chemical or mechanical bonding treatment may be used to form a bonded web such that a coherent web structure results. In the embodiment shown in FIG. 1, the web 11 is bonded by plurality of intermittent bonds, indicated by the reference character B. In this regard, thermal point bonding is most preferred. Various thermal point bonding techniques are known, with the most preferred utilizing calender rolls with a point bonding pattern. Any pattern known in the art may be used with typical embodiments employing continuous or discontinuous patterns. Preferably, the bonds B cover between 6 and 30 percent of the area of the web 11, more preferably 8 to 20 percent, and most preferably, 12 to 18 percent of the layer is covered. By bonding the web in accordance with these percentage ranges, the filaments are allowed to elongate throughout the full extent of stretching while the strength and integrity of the fabric is maintained.

Alternatively, the extensible coherent nonwoven web 11 can be a carded nonwoven web of staple fibers. As known, carding is typically carried out on a machine which utilizes opposed moving beds or surfaces of fine, angled, spaced apart teeth or wires to pull clumps of staple fibers into a web. Fibers within the web are then subjected to bonding to form a coherent web structure by any suitable thermal, chemical or mechanical bonding treatment. For example, thermal point bonds are formed in a manner previously described to impart strength and flexibility to the fabric.

In accordance with the invention, the staple fibers or continuous filaments which form the extensible web 11 are multipolymer fibers formed of at least two polymer components. For the purposes of the invention, the term "polymer" is used in a general sense, and is intended to include homopolymers, copolymers, grafted copolymers, and terpolymers. The term blend is also used generally herein, and is intended to include immiscible and miscible polymer blends. The polymers are considered to be "immiscible" if they exist in separate, distinct phases in the molten state; all other blends are considered to be "miscible". It is understood that varying levels of miscibility can exist, and are also intended to be within the scope of this invention. Blends with more than two polymers may also be utilized, including those with three or more polymer components. Both immiscible and miscible polymers may be added to a two component blend to impart additional properties or benefits with respect to blend compatibility, viscosity, polymer crystallinity or phase domain size.

Since the blends employed in the invention will undergo extrusion, stabilizers and antioxidants are conventionally added to the polymer blend. Other additives may also be added in accordance with the present invention. For example inorganic additives such as titanium dioxide, talc, fumed silica or carbon black. The blend may also contain other additives, such as other polymers, diluents, compatibilizers, antiblocking agents, impact modifiers, plasticizers, UV stabilizers, pigments, delusterants, lubricants, wetting agents, antistatic agents, nucleating agents, rheology modifiers, water and alcohol repellents, and the like. It is also anticipated that additive materials which have an affect on processing or product properties, such as extrusion, quenching, drawing, laydown, static and/or electrical properties, bonding, wetting properties or repellency properties may also be used in combination with the blend. In particular, polymeric additives may also be used in conjunction with the blends which impart specific benefits to either processing and/or end use.

According to one broad aspect of the invention, the multipolymer fibers are formed of a polymer blend composed of two or more polymers. The polymers of the blend can be miscible, immiscible, or a combination of miscible and immiscible polymers. In one embodiment in accordance with the invention, the polymers may exist as a dominant continuous phase and at least one substantially discontinuous dispersed phase. In the case where the blend exists as a dominant continuous phase and at least one discontinuous phase, other polymers may also be present which are either miscible in one, or the other, or both polymer phases.

According to a further aspect of the invention, the multipolymer fibers are formed of a polymer blend including a relatively low modulus polymer and at least one higher modulus polymer. It is believed that this combination is particularly valuable when the low modulus polymer is the dominant phase and the higher modulus polymer is dispersed therein. It is theorized that the higher modulus polymer acts to 'reinforce' the low modulus dominant phase, lending stability to spinning, and stiffening the web just enough to allow for higher bond temperatures while reducing the risk of the web sticking to and wrapping the calender. In the case of multipolymer fibers formed of an immiscible polymer blend it is believed that the small amount of the dispersed polymer may have the effect of wind up speed suppression (WUSS) on the dominant polymer phase as described by Brody in U.S. Pat. No. 4,518,744. Wind up speed suppression occurs when a small amount of an immiscible additive effectively reduces the degree of molecular orientation within the fiber at a given filament spinning velocity. The result is a filament with generally higher elongation and lower tenacity.

In yet another aspect of the invention, the multipolymer fibers are formed of a polymer blend composed of a dominant continuous phase, and at least one polymer, having low mutual affinity with the dominant phase, dispersed therein, and at least one additional polymer which is at least partially miscible in one or the other or both continuous and dispersed polymer phases. If the one additional polymer is miscible in the dominant phase, and effectively reduces its crystallinity, it is believed that the improved extensibility observed in the resulting composites may be due to an 'impact-modifying' effect. If the one additional polymer has an affinity for both polymers, or serves to lower the surface energies between the two phases, it is believed that the improvement observed in the composite extensibility is due to a compatibilization effect. Independent of theory, the blend must ultimately form filaments or fibers, which when formed into webs and composite structures exhibit the properties described by the invention, meaning low fuzz and good elongation.

In one embodiment, the multipolymer fibers may comprise from 1 to 50 percent by weight polyethylene and from 99 to 50 percent by weight propylene polymer. Fabrics formed from such blends exhibit low fuzz and good elongation.

In applications where tensile strength is particularly important and high elasticity is of lesser concern, the composite fabric may include a coherent, extensible nonwoven web 11 formed of fibers of a polyethylene—propylene polymer blend where the polyethylene is present in the range of 1% to 10% and the propylene polymer is present in the range of 90% to 99% by weight. In still another embodiment, very substantial and surprising increases in elongation can be achieved by blending a third polymer component into the blend. For example, the multipolymer fibers may include a dominant amount of a propylene polymer, such as isotactic polypropylene, a small amount of a polymer having low mutual affinity with the dominant polymer, such as polyethylene, and an additional third polymer which either reduces crystallinity and/or compatibilizes the blend. What results is a softer web, with extremely high extensibility. Preferred multipolymer fibers according to this embodiment may comprise greater than 50 percent by weight propylene polymer, 1 to 10 percent polyethylene, and 10 to 40 percent of the third polymer. Suitable additional third polymers include propylene copolymers and terpolymers such as the commercially available Catalloy™ copolymers available from Montell. These resins are characterized by having the comonomer(s) exist to some degree in blocks, and wherein at least some portion of the polymer chain is miscible with one or the other, or both, dominant and dispersed polymer phases. Other suitable polymers are the Reflex™ flexible polyolefins from Rexene. These crystallinity reducing resins are characterized as having atactic segments present in the polymer chain, such that the "tacticity" of the polymer is affected. Especially preferred multipolymer fibers according to this embodiment comprise 65 to 80 percent isotactic polypropylene, 1 to 5 percent polyethylene, and 15 to 30 percent of a polyolefin copolymer wherein at least a portion of the chain is miscible with isotactic polypropylene.

Another class of useful and advantageous products according to this aspect of the invention employ multipolymer fibers formed of a polymer blend comprised of a soft, extensible polymer phase, and at least one additional polymer having low mutual affinity with the soft, extensible phase, such that it modifies either the rheological, mechanical, and/or thermal properties of the fibers in a way that improves processability (e.g. melt spinning), bonding and/or abrasion resistance while maintaining high extensibility. In a preferred embodiment the soft, extensible phase is present as a dominant, continuous phase. For example, polyethylene can be used as the soft, extensible dominant phase and a propylene polymer as the additional modifying polymer. In a preferred embodiment the additional polymer is added in a small proportion relative to the dominant phase. In another preferred embodiment, the additional polymer exhibits higher viscosity relative to the dominant phase. Blending a relatively small proportion of the higher of viscosity propylene polymer, with the soft, extensible polyethylene polymer, imparts greatly increased abrasion resistance to a nonwoven fabric formed from the polymer blend, without significant adverse effect upon other important fabric properties, such as extensibility, softness, tensile strength, etc. The spinnability of the polyethylene is also improved by the presence of the additional propylene polymer. According to this embodiment, the fibers preferably comprise between 2 to 50 percent by weight of the propylene polymer, e.g. 3% ethylene-propylene copolymer, and 98 to 50 percent by weight of the soft, extensible polymer, e.g. polyethylene. In one particularly preferred embodiment, the fiber composition may range from 5 to 40 percent by weight propylene polymer, and most desirably between 5 to 25 percent by weight propylene polymer and 75 to 95 percent by weight polyethylene. Especially suited for applications requiring good extensibility, tensile strength and abrasion resistance are fiber compositions of from 5 to 25 percent by weight propylene polymer. A most preferred embodiment contains 5 to 25 percent by weight of ethylene-propylene copolymer or terpolymer and 75 to 95 percent by weight linear low density polyethylene. In these embodiments, the lower melting polyethylene is present as a substantially continuous phase in the blend and the higher melting propylene polymer is present as a discontinuous phase dispersed in the polyethylene phase.

In producing the fibers, the polyethylene and propylene polymer components are combined in appropriate proportional amounts and intimately blended before being melt-spun. In some cases sufficient mixing of the polymer components may be achieved in the extruder as the polymers are converted to the molten state.

Various types of polyethylene may be employed. As an example, a branched (i.e., non-linear) low density polyethylene or a linear low density polyethylene (LLDPE) can be utilized and produced from any of the well known processes, including metallocene and Ziegler-Natta catalyst systems. LLDPE is typically produced by a catalytic solution or fluid bed process under conditions established in the art. The resulting polymers are characterized by an essentially linear backbone. Density is controlled by the level of comonomer incorporated into the otherwise linear polymer backbone. Various alpha-olefins are typically copolymerized with ethylene in producing LLDPE. The alpha-olefins which preferably have four to eight carbon atoms, are present in the polymer in an amount up to about 10 percent by weight. The most typical comonomers are butene, hexene, 4-methyl-1-pentene, and octene. In general, LLDPE can be produced such that various density and melt index properties are obtained which make the polymer well suited for melt-spinning with polypropylene. In particular, preferred density values range from 0.87 to 0.95 g/cc (ASTM D-792) and melt index values usually range from 0.1 to about 150 g/10 min. (ASTM D1238-89, 190° C.). Preferably, the LLDPE should have a melt index of greater than 10, and more preferably 15 or greater for spunbonded filaments. Particularly preferred are LLDPE polymers having a density of 0.90 to 0.945 g/cc and a melt index of greater than 25. Examples of suitable commercially available linear low density polyethylene polymers include those available from Dow Chemical Company, such as ASPUN Type 6811 (27 MI, density 0.923), Dow LLDPE 2500 (55 MI, 0.923 density), Dow LLDPE Type 6808A (36 MI, 0.940 density), and the Exact series of linear low density polyethylene polymers from Exxon Chemical Company, such as Exact 2003 (31 MI, density 0.921).

Various propylene polymers made by processes known to the skilled artisan may also be employed. In general, the propylene polymer component can be an isotactic or syndiotactic propylene homopolymer, copolymer, or terpolymer. Examples of commercially available propylene homopolymers which can be used in the present invention include SOLTEX Type 3907 (35 MFR, CR grade), HIMONT Grade X10054-12-1 (65 MFR), Exxon Type 3445 (35 MFR), Exxon Type 3635 (35 MFR) AMOCO Type 10-7956F (35 MFR), and Aristech CP 350 J (melt flow rate approximately 35). Examples of commercially available copolymers of propylene include Exxon 9355 which is a random propylene copolymer with 3% ethylene, 35 melt flow rate; Rexene 13S10A, a 10 melt flow rate random propylene copolymer with 3% ethylene; Fina 7525MZ, an 11 melt flow rate 3% ethylene random propylene copolymer, Montel EPIX 30F, a 1.7% ethylene, 8 melt flow rate random copolymer of propylene. When the propylene polymer is the dominant continuous phase of the blend, the preferred melt flow rate is greater than 20. When the propylene polymer exists as the dispersed phase of the blend, the preferred melt flow rate is less than 15 and most preferably less than 10.

In still another embodiment, the multipolymer fibers of the web 11 may be bicomponent or multicomponent fibers or filaments. The term bicomponent or multicomponent refers to the existence of the polymer phases in discrete structured domains, as opposed to blends where the domains tend to be dispersed, random or unstructured. The polymer components can be configured into any number of configurations including sheath-core, side-by-side, segmented pie, islands-in-the-sea, or tipped multilobal. A coherent extensible nonwoven web can be made, for example, from a sheath-core bicomponent fiber having a polyester core and a polyethylene sheath. Alternatively, the extensible web 11 can comprise a single web containing a combination of spunbonded filament and meltblown fibers or a combination of carded staple fibers and meltblown fibers.

The extensible nonwoven web 11, in all embodiments in accordance with the present invention, is characterized by having high surface abrasion resistance and high elongation. The surface abrasion resistance of the web may be conveniently measured objectively by physical tests which are standard in the industry, such as the Taber abrasion test as defined by ASTM Test Method D-3884-80. Extensible webs useful in the composite fabrics of the present invention are characterized by having a Taber abrasion value (rubber wheel) of greater than 10 cycles. Webs useful in the composite fabrics of the present invention are further characterized by having an elongation at peak load (ASTM D-1682) in either the machine direction (MD) or in the cross-machine direction (CD) or both of at least 70 percent, more preferably at least 100 percent, and most desirably at least 150 percent. The multipolymer fibers of the web 11 are of relatively fine diameter, typically 10 denier or less.

The second extensible layer 12 of the composite fabric 10 can exist in various forms. According to one embodiment, it is a polyolefin film, most preferably a nonelastic polyolefin film that is extensible at least 100 percent of its original length. The film preferably has a basis weight within the range of 10 to 40 grams per square meter. The present invention is particularly applicable to extensible film/fabric composites where the film of the type conventionally used as the impermeable outer component of a disposable diaper.

The extensible layer 12 can also be an elastic layer of various forms including webs of bonded filaments, nets, films, foams, parallel arrays of filaments, and the like. Preferably, a film is employed. Such structures are produced by conventional methods known to the skilled artisan. For purposes of the present invention, an "elastic" layer is defined as having a 75% recovery after a single extension of 10% the original dimension. As also known, any suitable elastomeric forming resins or blends thereof may be utilized in producing the above structures. Such suitable materials include the diblock and triblock copolymers based on polystyrene (S) and unsaturated or fully hydrogenated rubber blocks. The rubber blocks can consist of butadiene (B), isoprene (I), or the hydrogenated version, ethylene-butylene (EB). Thus, S-B, S-I, S-EB, as well as S-B-S, S-I-S, and S-EB-S block copolymers can be used. Preferred elastomers of this type include the KRATON polymers sold by Shell Chemical Company or the VECTOR polymers sold by DEXCO. Other elastomeric thermoplastic polymers include polyurethane elastomeric materials such as ESTANE sold by B.F. Goodrich Company; polyester elastomers such as HYTREL sold by E.I. Du Pont De Nemours Company; polyetherester elastomeric materials such as ARNITEL sold by Akzo Plastics; and polyetheramide materials such as PEBAX sold by Elf Atochem Company; polyolefin elastomers such as Insite™, Affinity™ or Engage™ polyethylene plastomers from Dow Chemical or the Exact™ polyethylene plastomers available from Exxon Chemical. Crosslinked elastomers such as crosslinked urethanes and rubbers may also be employed. Blends of these polymers with other polymers, such as, for example, polyolefins may be employed to enhance processing such as decreasing melt viscosity, allowing for lower melt pressures and temperatures and/or increase throughput.

In accordance with the invention, the composite fabric 10 is formed by laminating nonelastic extensible web 11 and extensible web 12, with or without an adhesive, utilizing any of the well established thermal or chemical techniques including thermal point bonding, open-nip thermal lamination, through air bonding, needlepunching, and adhesive bonding, with adhesive bonding being preferred. A suitable adhesive, if desired, is applied either to web 11, to extensible web 12, or to both, as either a continuous or discontinuous coating, to form an adhesive layer 13. Where a continuous adhesive coating is employed, the adhesive layer 13 should be relatively thin and the adhesive should be sufficiently flexible or extensible to allow the filaments to elongate upon stretching. Where a discontinuous adhesive is employed, any intermittent pattern can be used such as, for example, lines, spirals, or spots, and the adhesive can be less extensible. The adhesive can be applied continuously or intermittently by any accepted method including spraying, slot coating, meltblowing and the like.

Suitable adhesives can be made from a variety of materials including polyolefins, polyvinyl acetate polyamides, hydrocarbon resins, waxes, natural asphalts, styrenic rubbers, and blends thereof. Preferred adhesives include those manufactured by Century Adhesives, Inc. of Columbus, Ohio and marketed as Century 5227 and by H.B. Fuller Company of St. Paul, Minn. and marketed as HL-1258.

In assembling the composite fabric 10, layers 11 and 12 are provided in an unstretched state from individual supply rolls. If desired, adhesive is then applied over the surface of extensible web 11 or layer 12. Soon after the adhesive is applied, the layers are subjected to pressure thus forming fabric 10. For example, the layers can be fed through calender nip rolls. Alternatively, the fabric can be bonded by thermal means with or without an adhesive.

In a further embodiment depicted in FIG. 2, the composite fabric 10' includes an additional component 14 on the side of extensible web 12 opposite layer 11 to form a trilaminate. This third component may or may not be extensible. Any suitable material may be employed in various forms such as, for example, woven or nonwoven material, films or composites, such as a film-coated nonwoven. In the particular embodiment shown in FIG. 2, the component 14 is a nonelastic extensible polymeric film. Typically, a thermoplastic polymer film is used with preferred polymers being polypropylene or polyethylene. Commercially desirable films includes those manufactured by Tredegar Industries, Inc. of Terre Haute, Ind. If the component 14 is substantially impervious to liquids, it can be suitably employed as a back sheet in personal garment applications such as diapers, training pants, incontinence briefs and feminine hygiene products. Any well known techniques for laminating component 14 to the composite structure may be utilized; preferably, component 14 is laminated by a thin layer 15 of adhesive in a manner previously described.

Alternatively, component 14 can be a nonwoven web, which can be constructed to be extensible or essentially nonextensible. For example, the nonwoven web may be another web of multipolymer fibers similar to web 11 so that a fibrous web is used on both faces of the composite fabric 10'. An essentially nonextensible nonwoven web can also be employed, such as a carded thermally point bonded web of low elongation fibers such as Hercules Type 196 polypropylene staple fibers.

Referring to FIG. 3, stretching forces are applied to composite fabric 10 to extend and elongate the fabric in the machine direction (MD) and/or cross-machine direction (CD). Numerous established techniques can be employed in carrying out this operation. For example, a common way for obtaining MD elongation is to pass the fabric through two or more sets of nip rolls, each set moving faster than the previous set. CD elongation may be achieved through tentering. Other means may be employed; for example, "ring rolling" as disclosed in U.S. Pat. No. 5,242,436 to Weil et al., incorporated herein by reference, is often used in obtaining CD and/or MD elongation.

Upon application of elongation forces (denoted by F) on fabric 10, fibers within extensible layer 11 oriented in the direction of the elongation experience tension and the fabric and fibers undergo deformation. During this process, the fibers are capable of elongating well beyond their unstretched length. As an example, fabric elongation between 70 and 300 percent is often realized. In most instances, the fibers are elongated past their elastic limit, undergo plastic deformation, and become permanently extended. In accordance with the invention, intermittent bonds B distributed throughout nonelastic layer 11 are of high strength such that fibers are sufficiently tied down within the nonelastic layer 11 and fiber detachment is minimized during the elongation process. Accordingly, fiber detachment is reduced with the desirable result that abrasion resistance is maintained and fuzzing is minimized. Moreover, fabric strength is maintained as the coherent web structure is kept intact during the elongation operation.

The fabric 10 is particularly well suited for use in various disposable garments such as diapers, training pants, incontinence briefs and feminine hygiene products. The fabric may be utilized in a diaper, such as the one illustrated in FIG. 4 (denoted as 20) having a waist region 21 and leg cuff components 22. Since the composite fabric 10 is both soft and strong, the diaper can withstand rigorous movement of the wearer without rubbing or chafing the wearer's skin during use.

The following examples serve to illustrate the invention but are not intended to be limitations thereon.

EXAMPLE 1

This example illustrates the benefits of various multipolymer systems in producing low fuzz, highly extensible spunbond nonwoven fabrics, and compares the fabric properties to a conventional spunbond fabric made of 100 percent isotactic polypropylene. Continuous filament spunbond nonwoven fabrics were produced under generally similar conditions from different multipolymer blend combinations, as follows: Sample A: a 26 g/m$^2$ spunbond fabric consisting of 96% isotactic polypropylene and 4% polyethylene (Dow 05862N); Sample B: a 33 g/m$^2$ spunbond fabric consisting of 76% isotactic polypropylene, 20% propylene copolymer (Montell KS057P), and 4% polyethylene (Dow 05862N); Sample C: a 33 g/m$^2$ spunbond fabric consisting of 85% polyethylene (Dowlex 2553) and 15% ethylene-propylene copolymer (Amoco 8352); and Sample D: a 60 g/m$^2$ spunbond-meltblown-spunbond composite fabric consisting of bicomponent spunbond filaments (polyester core, polyethylene sheath) and meltblown polyethylene. The fabric tensile strength and peak elongation properties were measured in the machine direction (MD) and in the cross-machine direction (CD) according to ASTM D-1682. The Taber abrasion resistance of the fabrics were measured according to ASTM D-3884, using both the rubber wheel test and the felt wheel test. The results are shown in Table 1, below. For comparison, a commercially available 100% isotactic polypropylene spunbond fabric produced by Fiberweb North America under the trademark Celestra®, was also tested, and reported in Table 1 as Sample E. It was not tested for fuzz, since it failed the elongation criteria.

TABLE 1

Physical Properties of High Elongation Multi-Polymer Nonwoven Fabrics

| Sample | Tensile MD (g/cm) | Tensile CD (g/cm) | Elong. MD (%) | Elong. CD (%) | Taber Abrasion (cycles) Rubber Wheel | Taber Abrasion (cycles) Felt Wheel |
|---|---|---|---|---|---|---|
| A | 1144 | 307 | 132 | 121 | 79 | 800 |
| B | 1325 | 578 | 215 | 191 | 71 | 1050 |
| C | 610 | 263 | 141 | 188 | 124 | 1300 |
| D | 1764 | 507 | 154 | 133 | 127 | 2650 |
| E | 768 | 553 | 38 | 44 | nt* | nt* |

*nt = not used. This material fails the elongation criteria and therefore was not tested for fuzz.

EXAMPLE 2

Ninety percent by weight of a linear low density polyethylene (LLDPE) with a melt flow of 27 (Dow 6811 LLDPE) and ten percent by weight of a polypropylene (PP) polymer with a melt flow approximately 35 (Aristech CP 350 J) were dry blended in a rotary mixer. The dry-blended mixture was then introduced to the feed hopper of an extruder of a spunbond nonwoven spinning system. Continuous filaments were meltspun by a slot draw process at a filament speed of approximately 600 m/min and deposited upon a collection surface to form a spunbond nonwoven web, and the web was thermally bonded using a patterned roll with 12% bond area. For comparison purposes, nonwoven spunbond fabrics were produced under similar conditions with the same polymers, using 100% PP and 100% LLDPE.

As shown in Table 2, the 100% LLDPE spunbond samples exhibited superior softness (75 and 77.5) compared to the 100% polypropylene spunbond sample (30). However, the abrasion resistance of the 100% LLDPE sample, as seen from the fuzz measurement, was relatively high (12.5 and 2.4) compared to the 100% PP sample (0.3). The nonwoven fabric formed from the 90% LLDPE/10%PP blend had a high softness (67.5) only slightly less than the 100% LLDPE fabric, and had abrasion resistance (fuzz value) of 1.0 mg., which is significantly better than the values seen for 100% LLDPE. The blend sample also showed improved CD tensile compared to products made with 100% LLDPE.

TABLE 2

| Sample | A | B | C | D |
|---|---|---|---|---|
| C = comparison  I = invention | C | C | C | I |
| Composition: | | | | |
| % polypropylene | 100 | 0 | 0 | 10 |
| % polyethylene | 0 | 100 | 100 | 90 |
| filament dia. (microns) | 17.5 | 20.9 | 20.9 | 22.5 |
| Basis weight (gsm)[1] | 23.1 | 25.2 | 24.6 | 24.8 |
| Loft @ 95 g/in² (mils)[2] | 9.8 | 9.0 | 7.8 | 9.3 |
| Fuzz (mg)[3] | 0.3 | 12.5 | 2.4 | 1.0 |
| Softness[4] | 30 | 75 | 77.5 | 67.5 |

TABLE 2-continued

| Sample | A | B | C | D |
|---|---|---|---|---|
| Strip Tensile (g/cm)[5] | | | | |
| CD | 557 | 139 | 157 | 164 |
| MD | 1626 | 757 | 639 | 467 |
| Peak Elongation (%) | | | | |
| CD | 90 | 116 | 129 | 108 |
| MD | 93 | 142 | 106 | 119 |
| TEA (in.g./in | | | | |
| CD | 852 | 297 | 346 | 354 |
| MD | 2772 | 2222 | 1555 | 1389 |

[1]gsm = grams per square meter
[2]Loft was determined by measuring the distance between the top and the bottom surface of the fabric sheet while the sheet was under compression loading of 95 grams per square inch. The measurement is generally the average of 10 measurements.
[3]Fuzz is determined by repeatedly rubbing a soft elastomeric surface across the face of the fabric a costant number of times. The fiber abraded from the fabric surface is then weighed. Fuzz is reported as mg weight observed.
[4]Softness was evaluated by an organoleptic method wherein an expert panel compared the surface feel of Example Fabrics with that of controls. Results are reported as a softness score with higher values denoting a more pleasing hand. Each reported value is for a single fabric test sample, but reflects the input of several panel members.
[5]Tensile, Peal Elongation and TEA were evaluated by breaking a one inch by seven inch long sample generally following ASTM D1682-64, the one-inch cut strip test. The instrument cross-head speed was set at 5 inches per minute and the gauge length was set at 5 inches per minute. The Strip Tensile Strength, reported as grams per centimeter, is generally the average of at least 8 measurements. Peak Elongation is the percent increase in length noted at maximum tensile strength. TEA, Total Tensile Energy Absorption, is calculated from the area under the stress-strain curve generated during the Strip Tensile test.

EXAMPLE 3 (Control)

A control fiber was made by introducing 100% Dow LLDPE 2500 (55 MI, 0.923 density) to a feed hopper of a spinning system equipped with an extruder, a gear pump to control polymer flow at 0.75 gram per minute per hole, and a spinneret with 34 holes of L/D=4:1 and a diameter of 0.2 mm. Spinning was carried out using a melt temperature in the extruder of 215° C. and a pack melt temperature of 232° C. After air quench, the resulting filaments were drawn down at a filament speed of approximately 1985 m/min using an air aspiration gun operating at 100 psig to yield a denier of 3.01 and denier standard deviation of 0.41.

EXAMPLE 4

Ninety parts by weight of Dow LLDPE Type 2500 (55 MI, 0.923 density) and ten parts of Himont X1005412-1 polypropylene (65 MFR) were dry blended in a rotary mixer and then introduced to the feed hopper of the spinning system described in Example 2. Spinning was carried out using a pack melt temperature of 211° C. After air quench, the resulting filaments were drawn down at a filament speed of approximately 2280 M/Min using an air aspiration gun operating at 100 psig to yield a denier of 2.96 and a denier standard deviation of 1.37.

EXAMPLE 5

Ninety parts by weight of Dow LLDPE Type 2500 (55 MI, 0.923 density) and ten parts of Soltex 3907 polypropylene (35 MFR, 1.74 die swell, CR grade) were dry blended in a rotary mixer and then introduced to the feed hopper of the spinning system described in Example 2. Spinning was carried out using a pack melt temperature of 231° C. and an extruder melt temperature of 216° C. After air quench, the resulting filaments were drawn down at a filament speed of approximately 2557 M/Min using an air aspiration gun operating at 100 psig to yield a denier of 2.64 and a denier standard deviation of 0.38.

EXAMPLE 6

Ninety parts by weight of Dow LLDPE Type 6808A (36 MI, 0.940 density) and ten parts of Soltex 3907 polypropylene (35 MFR, 1.74 die swell, CR grade) were dry blended in a rotary mixer and then introduced to the feed hopper of the spinning system described in Example 3. Spinning was carried out using a pack melt temperature of 231° C. and an extruder melt temperature of 216° C. After air quench, the resulting filaments were drawn down at a filament speed of approximately 2129 M/Min using an air aspiration gun operating at 100 psig to yield a denier of 3.17 and a denier standard deviation of 2.22.

The quality of spinning for a given formulation has been found to roughly correlate with the denier standard deviation. A reduced standard deviation suggests more stable or higher quality spinning. Thus it is unexpected and contrary to the teaching of the prior art that the blend using a 35 MFR polypropylene in Example 5 yielded a more stable spinning than seen with the corresponding LLDPE control in Example 3.

EXAMPLE 7

Eighty parts by weight of a linear low density polyethylene pellets of 55 melt index and 0.925 g/cc density and twenty parts by weight polypropylene pellets of 35 melt flow rate were dry blended in a rotary mixer. The dry-blended mixture was then introduced to the feed hopper of a spinning system equipped with an extruder with a 30:1 l/d ratio, a static mixer, and a gear pump for feeding the molten polymer to a heated melt block fitted with a spinneret. Filaments were extruded from the spinneret and drawn using air aspiration.

EXAMPLE 8

Samples of continuous filament spunbonded nonwoven webs were produced from blends of a linear low density polyethylene with a melt flow rate of 27 (Dow 6811A LLDPE) and a polypropylene homopolymer (Appryl 3250YR1, 27 MFR) in various blend proportions. Control fabrics of 100 percent polypropylene and 100 percent polyethylene were also produced under similar conditions. The fabrics were produced by melt spinning continuous filaments of the various polymers or polymer blends, attenuating the filaments pneumatically by a slot draw process, depositing the filaments on a collection surface to form webs, and thermally bonding the webs using a patterned calender roll with a 12 percent bond area. The fabrics had a basis weight of approximately 25 gsm and the filaments had an average mass/length of 3 dtex. The tensile strength and elongation properties of these fabrics and their abrasion resistance were measured, and these properties are listed in Table 3. As shown, the 100 percent polypropylene control fabric had excellent abrasion resistance, as indicated by no measurable fuzz generation; however the fabrics had relatively low elongation. The 100 percent polyethylene control fabric exhibited good elongation properties, but very poor abrasion resistance (high fuzz values and low Taber abrasion resistance) and relatively low tensile strength. Surprisingly, the fabrics of the invention made of blends of polypropylene and polyethylene exhibited an excellent combination of abrasion resistance, high elongation, and good tensile strength. It is noted that the CD elongation values of the blends actually exceeded that of the 100% polyethylene control. This surprising increase in elongation is believed to be attributable to the better bonding of the filaments of the blend as compared to the bonding achieved in the 100% polyethylene control, which resulted in the fabrics of the invention making good use of the highly elongatable filaments without bond failure.

EXAMPLE 9

Samples of continuous filament spunbonded nonwoven webs of basis weight approximately 25 grams/square meter were produced from blends of a linear low density polyethylene with a melt flow rate of 27 (Dow 6811A LLDPE) and a polypropylene homopolymer (either Appryl 3250 YR1 or Aristech CP350J) in various blend proportions. Control fabrics of 100 percent polypropylene and 100 percent polyethylene were also produced under similar conditions. The fabrics were produced by melt spinning continuous filaments of the various polymers or polymer blends, attenuating the filaments pneumatically by a slot draw process, depositing the filaments on a collection surface to form webs, and thermally bonding the webs using a patterned calender roll with a 12 percent bond area. The tensile strength and elongation properties of these fabrics and their abrasion resistance were measured, and these properties are listed in Table 3. As shown, the 100 percent polypropylene control fabric had excellent abrasion resistance, as indicated by no measurable fuzz generation; however the fabrics had very low elongation, thus limiting the utility of such fabrics in extensible film/fabric laminates. The 100 percent polyethylene control fabric exhibited excellent elongation properties, but very poor abrasion resistance (high fuzz values) and relatively low tensile strength. Surprisingly, the fabrics made of polypropylene/polyethylene blends exhibited an excellent combination of abrasion resistance, high elongation, and good tensile strength. The high filament elongation makes the fabrics well suited for use in an extensible film/fabric composite structure.

EXAMPLE 10

A polyethylene film of approximately 1.5 mil thickness, such as is used in a disposable diaper backsheet, was sprayed with an all purpose adhesive (Locktite Corporation) and was bonded by application of pressure to a 25 gsm spunbond fabric containing 15% polypropylene and 85% polyethylene, one of the nonwoven fabrics described in Example 9. The cross machine direction of the fabric coincided with the cross machine direction of the film. The composite fabric of film and polypropylene/polyethylene spunbond nonwoven was then extended to 200% extension in the CD direction, beyond the elastic limit of the spunbond fabric, by an Instron tensile tester. The resulting elongated composite fabric was found to exhibit reduced basis weight, desirable softness and drape properties, and was surprisingly free of detached fibers and lint, thus showing no unsightly fuzzed appearance. The extended composite fabric was thicker in appearance than its unextended precursor. The elongated fabric can be used as a diaper backside or diaper leg cuffs.

TABLE 3

MECHANICAL PROPERTIES OF POLYPROPYLENE (PP)/POLYETHYLENE (PE) BLEND FABRICS

| Fabric | MD Tensile (g/cm)[6] | CD Tensile (g/cm)[1] | MD Elong (%)[1] | CD Elong (%)[1] | Fuzz (mg)[7] | Taber Abrasion (cycles-rubber wheel)[8] | Taber Abrasion (cycles-felt wheel)[3] |
|---|---|---|---|---|---|---|---|
| 100% PP | 925 | 405 | 62 | 70 | 0.0 | 40 | 733 |
| 50/50 PP/PE | 1110 | 415 | 147 | 145 | 0.3 | — | — |
| 25/75 PP/PE | 764 | 273 | 170 | 190 | 0.3 | 32 | 200 |
| 15/85 PP/PE | 676 | 277 | 199 | 224 | 0.5 | 22 | 500 |
| 10/90 PP/PE | 426 | 170 | 109 | 141 | 0.3 | — | — |
| 100% PE | 296 | 63 | 168 | 131 | 19.0 | 10 | 15 |

[6]Tensile and Peak Elongation were evaluated by breaking a one inch by seven inch long sample generally following ASTM D1682-64, the one-inch cut strip test. The instrument cross-head speed was set at 5 inches per minute and the gauge length was set at 5 inches per minute. The Strip Tensile Strength, reported as grams per inch, is generally the average of at least 8 measurements. Peak Elongation is the percent increase in length noted at maximum tensile strength.

[7]Fuzz is determined by repeatedly rubbing a soft elastomeric surface across the face of the fabric a constant number of times. The fiber abraded from the surface is then weighed. Fuzz is reported as mg weight observed.

[8]Conducted according to ASTM D3884-80 where the number of cycles was counted until failure. Failure was defined as the appearance of a hole of one square millimeter or greater in the surface of the fabric.

EXAMPLE 11

Figure 5B:
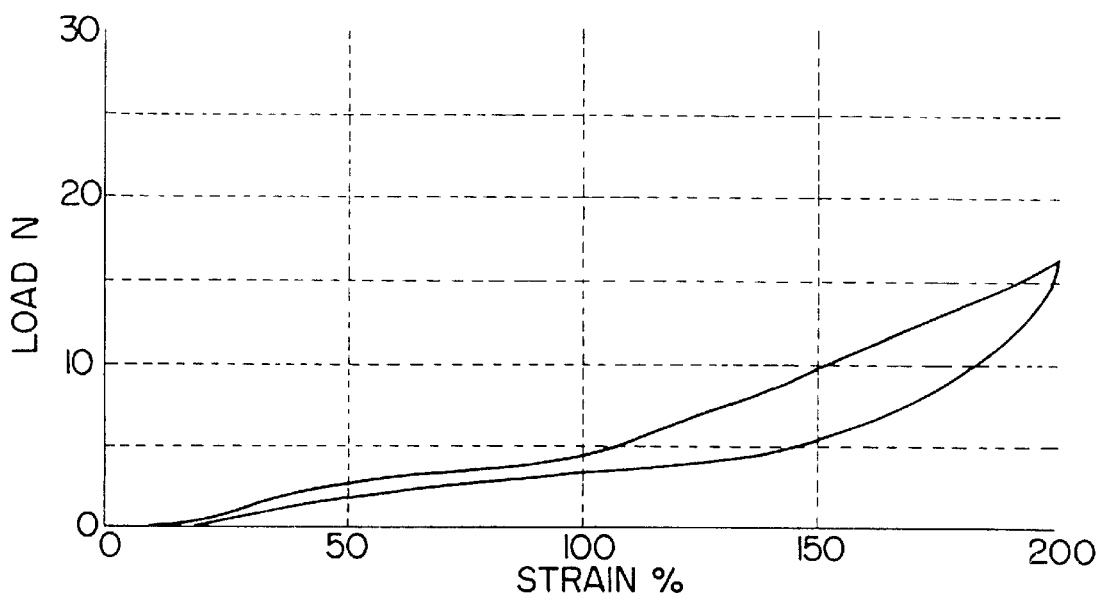

An elastic film of 1.5 mil thickness was cast from Hytrel 8122 polyester elastomer sold by E.I. Du Pont DeNemours Company. A sample of the elastic film was sprayed with an all purpose adhesive (Locktite Corporation) and was bonded by application of pressure to a 25 grams per square meter spunbonded fabric containing 15% polypropylene and 85% polyethylene (one of the nonwoven fabric samples described in Example 9). The cross machine direction of the fabric coincided with the machine direction of the film. A 1.5 inch wide sample of the resulting composite was placed in the jaws of an Instron tensile tester and elongated to 200% extension. The composite was returned to 0% extension. The resulting stress-strain curve is given in FIG. 5A. The spunbonded component remained attached to the elastic film but the filaments were elongated, so that the unextended composite had a bulky appearance. The composite was elongated a second time to 200% extension and then returned to 0% extension. The resulting stress-strain curve is given in FIG. 5B. The modulus of elasticity was much lower for the second extension, because the filaments of the spunbonded component were no longer resisting the extension. The composite had stretch behavior characteristic of an elastic material.

EXAMPLE 12

A fabric of the invention (Fabric A) was prepared by thermal point bonding three polyolefin webs placed in juxtaposition. These webs were melt spun from the following polymers:

Outer layer #1—8.5 grams per square meter 96% polypropylene (Exxon 3445)/4% polyethylene (Dow 05862N)

Middle Layer—2 grams per square meter 100% polypropylene (Exxon 3546G) meltblown fibers Outer layer #2—8.5 grams per square meter 96% polypropylene (Exxon 3445)/4% polyethylene (Dow 05862N)

The average fiber size in the outer layers was 3.3 dtex. The average fiber diameter in the middle layer was 1.9 microns.

The webs were bonded using a set of calender rolls with 17% bond area. The mechanical properties of this fabric, as well as those of a control fabric made of 100% polypropylene (Fabric B) are given in Table 3. The higher elongation of the fabric containing polyethylene in the filaments of the outer layers is clearly evident.

A sample of this trilaminate fabric (Fabric A) is inserted as a barrier cuff component into a diaper of the design described in U.S. Pat. No. 4,738,677. This diaper also incorporates a fastening system as described in U.S. Pat. No. 5,242,436. In this diaper, the above polyolefin trilaminate (Fabric A) is adhesively attached to a section of elastic foam in the side panel region of the diaper. The resulting elastic laminate is subjected to 33% extension. The thermal point thermal bonds of the inelastic trilaminate component remain intact while the filaments connecting the bonds are elongated. The result is that the side panel section of the diaper becomes stretchable, the elastic foam dominating its stress-strain characteristics.

EXAMPLE 13

Spunbond-meltblown-spunbond trilaminate fabrics were produced using spunbond outer webs of continuous filament multipolymer fibers of 4% polyethylene and 96% polypropylene and an inner extensible web of polypropylene meltblown microfibers having a maximum fiber diameter of 5 microns. The composite fabric was bonded by passing it through a heated calender at a temperature of 145° C. with the patterned roll of the calender producing a bond area of about 17 percent. The trilaminate fabrics were tested for tensile properties and the barrier properties of the composites were measured by a rising water column strikethrough test. The results are shown in Table 4.

TABLE 4

| Sample | F | G | H | I |
|---|---|---|---|---|
| Total basis weight (g/m$^2$) | 19.21 | 20.2 | 23.45 | 22.1 |
| Thickness (mm) | 0.18 | | 0.22 | |

TABLE 4-continued

| Sample | | F | G | H | I |
|---|---|---|---|---|---|
| | | 1 | | | |
| Spunbound denier (dpf) | top | 3.5 | 3.0 | 3.0 | 3.3 |
| | bottom | 3.0 | | 3.5 | |
| Meltblown fiber dia. | top | 1.95 | | 1.69 | |
| (microns) | bottom | 1.74 | | 1.75 | |
| Tensile strength (g/in) | MD | 1828 | 1439.0 | 1836.0 | 1504.0 |
| | CD | 424.4 | 512.4 | 530.7 | 588.8 |
| Max. elongation (%) | MD | 97.9 | 113.6 | 100.5 | 97.8 |
| | CD | 82.0 | 95.9 | 81.1 | 82.2 |
| Break elongation (%) | MD | 113.5 | 127.9 | 116.3 | 108.3 |
| | CD | 116.5 | 135.8 | 105.5 | 114.2 |
| TEA (cm-g/cm$^2$) | MD | 627.6 | 526.0 | 648.4 | 485.4 |
| | CD | 123.2 | 201.2 | 151.1 | 203.2 |
| Rising water column (MM) | | 111.9 | 11.6 | 209.9 | 246 |

The invention has been described in considerable detail with reference to its preferred embodiments. However, it will be apparent that numerous variations and modifications can be made without departure from the spirit and scope of the invention as described in the foregoing specification and defined in the appended claims.

That which we claim:

1. A composite nonwoven fabric of at least two layers, said composite fabric comprising at least one layer containing multipolymer fibers bonded by a plurality of bonds to form a coherent extensible nonwoven web, said coherent extensible nonwoven web having a Taber surface abrasion value (rubber wheel) of greater than 10 cycles and an elongation at peak load in at least one of the machine direction or the cross-machine direction of at least 70 percent, and said composite fabric comprising a second extensible layer attached to said coherent extensible nonwoven web.

2. A composite nonwoven fabric according to claim 1, wherein said coherent extensible web of multipolymer fibers has been permanently elongated by mechanical stretching.

3. A nonwoven fabric according to claim 1, wherein said extensible nonwoven web has an elongation at peak load of at least 100 percent.

4. A nonwoven fabric according to claim 1, wherein said bonds are thermal point bonds and comprise between 6 and 30 percent of the area of the extensible nonwoven web.

5. A nonwoven fabric according to claim 1, further comprising an adhesive layer disposed between said coherent extensible nonwoven web and said second extensible layer laminating the coherent extensible nonwoven web to said second extensible layer to form the composite fabric.

6. A nonwoven fabric according to claim 1, wherein said coherent extensible nonwoven web comprises a thermally bonded spunbond nonwoven web of randomly arranged substantially continuous filaments.

7. A nonwoven fabric according to claim 1, wherein said coherent extensible nonwoven web comprises a thermally bonded carded web of staple fibers.

8. A nonwoven fabric according to claim 6 or 7 wherein said coherent extensible nonwoven web additionally includes meltblown microfibers.

9. A nonwoven fabric according to claim 1, wherein said second extensible layer comprises a spunbonded web of continuous filaments.

10. A nonwoven fabric according to claim 1, wherein said second extensible layer comprises a web of meltblown microfibers.

11. A nonwoven fabric according to claim 1, wherein said second extensible layer comprises an elastic web.

12. A nonwoven fabric according to claim 11, wherein said elastic web comprises an elastic film, and said coherent extensible web of multipolymer fibers has been permanently elongated by mechanical stretching and the composite fabric exhibits elastic properties.

13. A nonwoven fabric according to claim 1, wherein said second extensible layer comprises a polyolefin film.

14. A nonwoven fabric according to claim 13, wherein said coherent extensible web of multipolymer fibers has been permanently elongated by mechanical stretching.

15. A nonwoven fabric according to claim 1, additionally comprising a third component laminated to said second extensible layer or to said coherent extensible nonwoven web.

16. A nonwoven fabric according to claim 15 wherein said third component comprises a coherent extensible nonwoven web comprised of a layer of multipolymer fibers bonded by a plurality of bonds.

17. A nonwoven fabric according to claim 15 wherein said third component is an extensible film.

18. A nonwoven fabric according to claim 15 wherein said third component is a relatively nonextensible nonwoven web.

19. A nonwoven fabric according to claim 1, wherein said multipolymer fibers are formed of a blend of at least two polymers.

20. A nonwoven fabric according to claim 19, wherein said blend of at least two polymers is a blend of at least two immiscible polymers.

21. A nonwoven fabric according to claim 19, wherein said blend of at least two polymers is a blend of at least two miscible or partially miscible polymers.

22. A nonwoven fabric according to claim 19, wherein said blend of at least two polymers is a blend of at least one immiscible polymer and at least one additional miscible or partially miscible polymer.

23. A nonwoven fabric according to claim 20 or 22, wherein said immiscible blend is comprised of a dominant, continuous phase and at least one dispersed phase.

24. A nonwoven fabric according to claim 19, wherein said polymer blend comprises a propylene polymer and polyethylene.

25. A nonwoven fabric according to claim 24, wherein said polyethylene is linear low density polyethylene and said propylene polymer is a propylene copolymer or terpolymer.

26. A nonwoven fabric according to claim 24, wherein said polyethylene is a linear low density polyethylene polymer of a melt index of greater than 10 and a density of less than 0.945 g/cc and said propylene polymer is a copolymer of propylene with up to 5 percent by weight ethylene.

27. A nonwoven fabric according to claim 24, wherein said polyethylene and said propylene polymer are present as distinct phases in the fiber, the propylene polymer being present as the dominant polymer and forming a substantially continuous phase, and said polyethylene being present in an amount less than said dominant polymer and being dispersed in said continuous phase.

28. A nonwoven fabric according to claim 27 wherein said polymer blend comprises 1 to 15 percent by weight polyethylene and 85 to 99 percent by weight propylene polymer.

29. A nonwoven fabric according to claim 22, wherein said blend comprises propylene polymer, polyethylene, and at least one additional miscible or partially miscible polymer.

30. A nonwoven fabric according to claim 29, wherein said additional miscible or partially miscible polymer is a polyolefin.

31. A nonwoven fabric according to claim 30, wherein said polymer blend comprises at least 50% isotactic polypropylene, 1 to 10% polyethylene, and 10 to 40% of said miscible or partially miscible polyolefin, and wherein said partially miscible polyolefin is a block or grafted copolymer.

32. A nonwoven fabric according to claim 30, wherein said polymer blend comprises 65 to 80% isotactic polypropylene, 15 to 30% of said miscible or partially miscible polyolefin, and 1 to 5% polyethylene.

33. A nonwoven fabric according to claim 24, wherein said fibers comprise between 2 to 50 percent by weight polypropylene and 50 to 98 percent by weight polyethylene.

34. A nonwoven fabric according to claim 24, wherein said fibers comprise from 5 to 25 percent by weight ethylene propylene copolymer of a melt index of 20 g/10 min. or less and 75 to 95 percent by weight linear low density polyethylene.

35. A nonwoven fabric according to claim 1, wherein said multipolymer fibers comprise at least two polymer components arranged into structured domains.

36. A nonwoven fabric according to claim 35, wherein said multipolymer fibers are bicomponent fibers with the polymer components thereof arranged in a sheath-core structured domain.

37. A nonwoven fabric according to claim 36, wherein said bicomponent fibers have a polyethylene sheath.

38. A nonwoven fabric according to claim 1, wherein said coherent extensible nonwoven web comprises a thermally bonded spunbond nonwoven web of randomly arranged substantially continuous filaments, and additionally includes meltblown microfibers, and wherein said substantially continuous filaments of said spunbond web have a fineness of 5 denier per filament or less, said meltblown microfibers have a fiber diameter of 5 microns or less.

39. A nonwoven fabric according to claim 38, which is of a spunbond-meltblown-spunbond construction and comprises an additional coherent extensible nonwoven spunbond web of randomly arranged substantially continuous filaments.

40. A composite nonwoven fabric comprising a coherent nonwoven extensible spunbonded web of randomly arranged substantially continuous filaments formed from a blend of 5 to 50 percent by weight propylene polymer and 50 to 95 percent by weight polyethylene, said coherent extensible nonwoven web having a Taber surface abrasion value (rubber wheel) of greater than 10 cycles and an elongation at peak load in at least one of the machine direction or the cross-machine direction of at least 70 percent, an additional extensible layer, and an adhesive disposed between said coherent extensible spunbond web and said additional extensible layer, said adhesive assisting in the connectivity between the spunbond web and the extensible layer.

41. A composite nonwoven fabric comprising a coherent nonwoven extensible spunbonded web of randomly arranged substantially continuous filaments formed from a blend of 85 to 99 percent by weight propylene polymer and 1 to 15 percent by weight polyethylene, said coherent extensible nonwoven web having a Taber surface abrasion value (rubber wheel) of greater than 10 cycles and an elongation at peak load in at least one of the machine direction or the cross-machine direction of at least 70 percent, an additional extensible layer, and an adhesive disposed between said coherent extensible spunbond web and said additional extensible layer, said adhesive assisting in the connectivity between the spunbond web and the extensible layer.

42. A composite nonwoven fabric comprising a coherent nonwoven extensible spunbonded web of randomly arranged substantially continuous filaments formed from a blend of 65 to 80 percent by weight isotactic polypropylene, 15 to 30 percent by weight of a polymer miscible or partially miscible with isotactic polypropylene, and 1 to 5 percent by weight polyethylene, an additional extensible layer, said coherent extensible nonwoven web having a Taber surface abrasion value (rubber wheel) of greater than 10 cycles and an elongation at peak load in at least one of the machine direction or the cross-machine direction of at least 70 percent, and an adhesive disposed between said coherent extensible spunbond web and said additional extensible layer, said adhesive assisting in the connectivity between the spunbond web and the extensible layer.

43. A composite nonwoven fabric comprising a coherent nonwoven extensible spunbonded web of randomly arranged substantially continuous filaments formed from bicomponent or multicomponent filaments, said coherent extensible nonwoven web having a Taber surface abrasion value (rubber wheel) of greater than 10 cycles and an elongation at peak load in at least one of the machine direction or the cross-machine direction of at least 70 percent, an additional extensible layer, and an adhesive disposed between said coherent extensible spunbond web and said additional extensible layer, said adhesive assisting in the connectivity between the spunbond web and the extensible layer.

44. A nonwoven fabric according to any one of claims 40 to 43, wherein said additional extensible web comprises a polyolefin film having an extensibility of at least 100 percent.

45. A nonwoven fabric according to any one of claims 40 to 43, wherein said additional extensible web comprises an elastic polyolefin film having an elastic recovery of at least 75 percent when elongated 10%.

46. A personal care product comprising the composite nonwoven fabric of claim 1.

47. A disposable diaper comprising the composite nonwoven fabric of any claim.

48. A nonwoven fabric comprising at least one layer containing multipolymer fibers bonded by a plurality of bonds to form a coherent extensible nonwoven web, said coherent extensible nonwoven web having a Taber surface abrasion value (rubber wheel) of greater than 10 cycles and an elongation at peak load in at least one of the machine direction or the cross-machine direction of at least 70 percent, and said multipolymer fibers comprising a blend of at least two polymers which are immiscible with one another and at least one additional polymer which is miscible or partially miscible with said immiscible polymers.

49. A nonwoven fabric according to claim 48, wherein said blend of immiscible polymers is comprised of a dominant, continuous phase and at least one dispersed phase.

50. A nonwoven fabric according to claim 49, wherein said blend of immiscible polymers comprises a propylene polymer and polyethylene.

51. A nonwoven fabric according to claim 50, wherein said polyethylene is linear low density polyethylene and said propylene polymer is a propylene copolymer or terpolymer.

52. A nonwoven fabric according to claim 51, wherein said polyethylene is a linear low density polyethylene polymer of a melt index of greater than 10 and a density of less than 0.945 g/cc and said propylene polymer is a copolymer of propylene with up to 5 percent by weight ethylene.

53. A nonwoven fabric according to claim 51, wherein said polyethylene and said propylene polymer are present as distinct phases in the fiber, the propylene polymer being present as the dominant polymer and forming a substantially continuous phase, and said polyethylene being present in an amount less than said dominant polymer and being dispersed in said continuous phase.

54. A nonwoven fabric according to claim 48, wherein said two polymers which are immiscible with one another comprise a propylene polymer and polyethylene, and wherein said at least one additional polymer is miscible or partially miscible with said propylene polymer and said polyethylene.

55. A nonwoven fabric according to claim 54, wherein said additional miscible or partially miscible polymer is a polyolefin.

56. A nonwoven fabric according to claim 54, wherein said polymer blend comprises at least 50% isotactic polypropylene, 1 to 10% polyethylene, and 10 to 40% of said miscible or partially miscible polymer, and wherein said partially miscible polymer is a block or grafted polyolefin copolymer or terpolymer.

57. A nonwoven fabric according to claim 56, wherein said polymer blend comprises 65 to 80% isotactic polypropylene, 15 to 30% of said miscible or partially miscible polyolefin, and 1 to 5% polyethylene.

58. A nonwoven fabric comprising at least one layer containing multipolymer fibers bonded by a plurality of bonds to form a coherent extensible nonwoven web, and said multipolymer fibers comprising a blend of at least 50% isotactic polypropylene, 1 to 10% polyethylene, and 10 to 40% of a block or grafted polyolefin copolymer or terpolymer which is miscible or partially miscible with said polypropylene and said polyethylene.

59. A nonwoven fabric according to claim 58, wherein said polymer blend comprises 65 to 80% isotactic polypropylene, 1 to 5% polyethylene, and 15 to 30% of said block or grafted polyolefin copolymer wherein at least a portion of the chain thereof is miscible with isotactic polypropylene.

60. A fiber useful for forming a nonwoven fabric, said fiber comprising a blend of at least 50% isotactic polypropylene, 1 to 10% polyethylene, and 10 to 40% of a block or grafted polyolefin copolymer or terpolymer which is miscible or partially miscible with said polypropylene and said polyethylene.

61. A fiber according to claim 60, wherein said polymer blend comprises 65 to 80% isotactic polypropylene, 1 to 5% polyethylene, and 15 to 30% of said block or grafted polyolefin copolymer wherein at least a portion of the chain thereof is miscible with isotactic polypropylene.

\* \* \* \* \*